United States Patent [19]

Spehr et al.

[11] Patent Number: 5,129,404
[45] Date of Patent: Jul. 14, 1992

[54] IMPLANTABLE ENDOCARDIAL LEAD WITH RETRACTABLE FIXATION APPARATUS

[75] Inventors: Paul R. Spehr; Arthur J. Foster, both of Lake Jackson, Tex.

[73] Assignee: Intermedics, Inc., Angleton, Tex.

[21] Appl. No.: 635,760

[22] Filed: Dec. 21, 1990

[51] Int. Cl.$^5$ ................................................. A61N 1/05
[52] U.S. Cl. ...................................... 128/785; 128/786
[58] Field of Search ........................ 128/784, 785, 786

[56] References Cited

U.S. PATENT DOCUMENTS 4,217,913  8/1980  Dutcher .............................. 128/785
5,003,992  4/1991  Holleman et al. ................... 128/785

Primary Examiner—William E. Kamm
Assistant Examiner—Scott M. Getzow
Attorney, Agent, or Firm—John R. Merkling

[57] ABSTRACT

An implantable endocardial lead with retractable sharpened helix. The piston has a central bore for receiving a specialized stylet. The stylet comprises a flexible wire having an enlarged distal end or tip. An elastomeric sliding sleeve fits over the wire. When the proximal end of the stylet is inserted into the bore in the piston, the wire can be withdrawn slightly, pulling the enlarged tip into the tube, and wedging the tube against the walls of the bore. By manipulating the stylet, the helix can be exposed outside of the lead, or retractable into the lead, as desired.

10 Claims, 1 Drawing Sheet

IMPLANTABLE ENDOCARDIAL LEAD WITH RETRACTABLE FIXATION APPARATUS

BACKGROUND OF THE INVENTION

1. Field of the Invention

The present invention relates generally to cardiac stimulation, and more particularly to an implantable endocardial lead which stimulates or senses electrical activity of the heart and which employs a retractable fixation mechanism which can be repeatedly exposed to or shielded from tissue during the process of securing the lead to cardiac tissue.

2. Prior Art

There are generally two types of body implantable leads used with cardiac pacemakers—one which requires surgery to expose the myocardial tissue to which an electrode is affixed and another which can be inserted through a body vessel, such as a vein, into the heart wherein an electrode contacts the endocardial tissue. In the latter type, the endocardial lead is often secured to the heart through the endothelial lining by a sharpened helix affixed to a distal end of the lead. When the end of the lead contacts the lining of the heart at a desired location, the lead may be secured in place by rotating the lead, thus screwing the helix into the heart tissue.

A helix system has been relatively effective in securing an endocardial lead once the initial location of the lead has been achieved. However, it is undesirable to expose the sharpened helix while the lead is being inserted through a blood vessel into the heart. Moreover, it is difficult to precisely place an endocardial lead on the first attempt. It is common for a physician to repeatedly attempt to place an endocardial lead having a sharpened helix securing means. It is desireable, therefore, to be able to shield the sharpened helix during the insertion of the lead through the vein and between attempts to implant the lead on the heart lining.

In the prior art, various apparatus have been proposed for achieving the desired result. For example, U.S. Pat. No. 3,974,834 to Lawrence M. Kane, discloses an implantable intervascular lead having an accordion-fold sleeve surrounding a helix. The sleeve is retractable to expose the helix and re-expandable to cover the helix in the event the helix is unscrewed and withdrawn. An object of the invention is to permit the lead to be inserted into and guided through a body vessel without snagging the body vessel.

Another attempt at solving these problems is disclosed in U.S. Pat. No. 4,146,036 to Robert G. Dutcher and Albert S. Benjamin. This patent discloses a body implantable, intervascular lead, having a helix fixation means. Apparatus for shielding the helix comprises a moveable piston or shaft located within the coils of the helix. The shaft is spring-loaded in a retracted position by the action of an elastomeric boot which also serves to seal off body fluids from the interior of the lead. A stylet passes through a lumen in the lead and acts against a proximal end of the shaft to force the shaft forward through the helix thus forming a partial barrier and inhibiting the helix from coming in contact with tissue, at least in the axial direction.

In U.S. Pat. No. 4,649,938 to William A. McArthur, an endocardial lead with an extendible/retractable helix fixation means is described. The helix is mounted on a bobbin carried within the electrode tip. The bobbin and helix are retracted into the electrode tip by the action of a spring and are extended out of the tip by pressure from the end of the stylet inserted through a lumen in the lead.

In U.S. Pat. No. 5,056,516 to Paul R. Spehr, one of us described an endocardial lead with a flexible, tubular lanyard. The lanyard passed through a lumen from a proximal end of the lead to a distal end of the lead, where the lanyard was attached to a sliding member supporting a helix. When the helix was in an exposed position, torque could be transmitted from the proximal end of the lanyard to the distal end thereof through a piston and thence to the helix to screw the helix into the endocardial tissue. To stiffen the lead during implantation, a stylet could be inserted into the lumen in the lanyard. The invention of this later patent has been assigned to the same assignee as our present invention. The patent was designated as an improvement on an invention of James I. Bradshaw, assigned to our same assignee and disclosed in U.S. Pat. No. 4,913,164.

SUMMARY OF THE INVENTION

The present invention provides an implantable endocardial lead with retractable fixation means. In the preferred embodiment, the fixation means comprises a sharpened helix which can be repeatedly both retracted within an electrode at a distal end of the lead and displaced outside the electrode. The lead defines an lumen from its proximal to its distal end. A specialized stylet can be inserted into the lumen at the proximal end and passed through the lead to the distal end. Located at the distal end of the lead is a piston supporting a sharpened helix. The piston can be either free to rotate with respect to the lead, or constrained to slide along the axis of the lead. The piston has a central bore for receiving the specialized stylet.

The stylet comprises a flexible wire having an enlarged distal end or tip. An elastomeric sliding sleeve, preferably of polyamide, fits over the wire. When the proximal end of the stylet is inserted into the bore in the piston, the wire can be withdrawn slightly, pulling the enlarged tip into the tube, and wedging the tube against the walls of the bore. By manipulating the stylet, the helix can be exposed outside of the lead or retracted into the lead, as desired.

It is a principal object of our present invention to provide an implantable endocardial lead with retractable fixation means wherein the fixation means can be repeatedly shielded and exposed during the implantation process.

A further object of our invention is to provide a lead wherein the fixation means is selectively shielded within an electrode located at the distal end of the lead and wherein the fixation means is selectively exposed and shielded by the action of a two-part, removable stylet.

These and other objects and features of our invention will be apparent from the detailed description taken with reference to the accompanying drawings.

DETAILED DESCRIPTION OF THE PREFERRED EMBODIMENT

Figure 1:
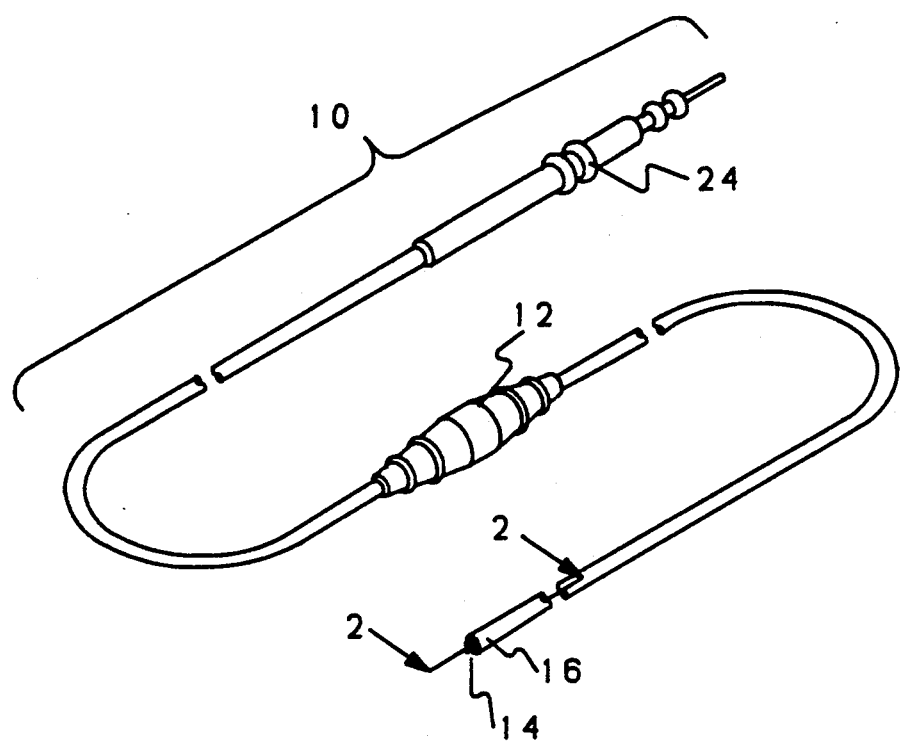
FIG. 1 is a prospective view of an implantable endocardial lead according to our invention.

Reference is now made to the drawings, wherein like numerals designate like parts throughout. FIG. 1 shows an endocardial lead, generally designated 10. The lead 10 has a suture sleeve 12 which slides along the lead 10 and which can be attached at an entrance into a vein of a patient in a conventional manner. The lead 10 also has an electrode 14 located at a distal end 16 of the lead.

Figure 2:
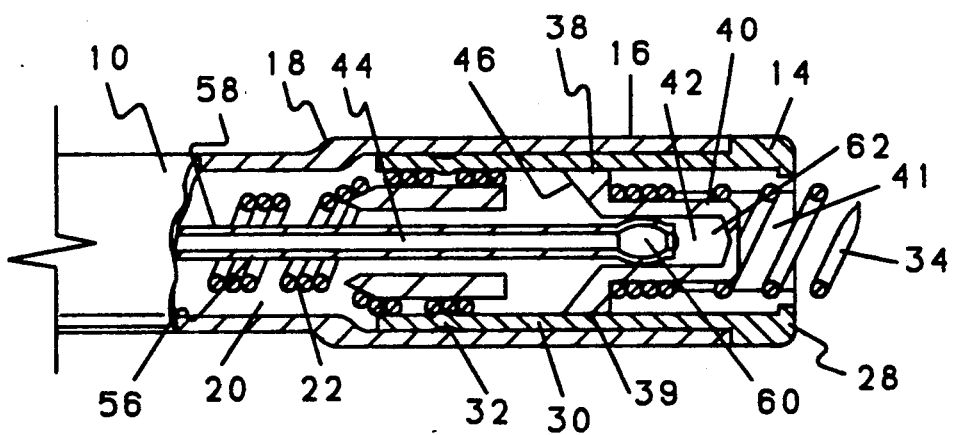
FIG. 2 is a sectional view of a distal tip of the lead taken along line 2—2 of FIG. 1.

As shown in FIG. 2, the lead 10 comprises a silicon or polyurethane sheath 18 which defines a lumen 20 along a longitudinal axis of the lead 10. Within the lumen 20, there is a coil conductor 22 for transmitting electrical impulses between the electrode 14 and a proximal end 24 of the lead 10. In the illustrated embodiment, a trifilar conductor is shown as the coil conductor 22. The coil conductor 22 wraps around a crimp slug 26 at the distal end 16 of the lead 10.

The electrode 14 comprises a ring contact 28 and a conductive sleeve 30. The conductive sleeve 30 fits over the crimp slug 26 and the coil conductor 22 and the three elements just mentioned are secured together by a crimp 32 in the conductive sleeve 30. The sheath 18 encloses the conductive sleeve 30 of the electrode 14 to the ring contact 28.

In the illustrated embodiment, a fixation means is illustrated by a sharpened helix 34. A piston 36 supports the helix 34 in relatively constant alignment along the longitudinal axis of the lead 10. The piston 36 comprises a sliding member 38 which slidably engages the conductive sleeve 30. On the distal side of the piston 36, the sliding member 38 forms an cylinder 40 on which the helix 34 is mounted.

In our preferred embodiment, the sliding member 38 has an hexagonal outer edge 39 which engages an hexagonal inner edge 41 of the electrode 14. This permits the helix 34 to be rotated by rotating the entire lead. However, it is equally possible to omit this feature and permit the piston to rotate inside the electrode. Torque would be applied to the helix through a stylet, to be described hereafter. Such a configuration would be especially well adapted for use in atrial leads, which frequently have a "J" shape which prevents the entire lead from being turned. The piston further comprises an interior bore 42 for receiving a stylet 44. At the proximal side of the piston 36 we have provided a chamfered edge 46 so that the lanyard 44 can be repeatedly inserted into the piston.

The stylet 44 passes through the lumen 20 in the lead 10 from the proximal end 24 to the distal end 16 thereof. In our preferred embodiment, the stylet 44 comprises a flexible wire 56 within a tube 58 of elastomeric material. Preferably the tube is comprised of a material such as polyamide which is relatively incompressible and inextensible but flexible. The wire 56 has an enlarged distal tip 60. In our preferred embodiment, the enlarged tip 60 is formed by soldering additional metal onto the end of the wire. An enlarged tip could also be formed by other means, such as flattening the wire. The outer diameter of the flattened section should be comparable to the outer diameter of the tube 58 and both should be sized to fit relatively easily into the bore 42 in the piston 36. The enlarged tip 60 should taper to the diameter of the wire 56 on at least the proximal side of the tip so that the tip can be forced into the tube with a wedging action whereby the stylet can be made to grip interior walls 62 of the bore 42.

During implantation, the sharpened helix 34 can be repeatedly moved into and out of the electrode 14 until proper placement has been achieved. Then the physician can withdraw the stylet 44. The stylet 44 can be replaced in the lead or withdrawn therefrom as often as desired. It can also be replaced in the lead after the lead has be implanted for a period of time, should it become necessary to reposition the lead and if it is desired to retract the sharpened helix within the lead.

Our invention may be embodied in other specific forms without departing from the spirit or essential characteristics thereof. The present embodiment is therefore considered in all aspects as illustrative and not restrictive, the scope of the invention being indicated by the appended claims rather than by the foregoing description, and all changes which come within the meaning and range of equivalency of the claims are therefore intended to be embraced therein.

We claim as our invention:

1. A lead assembly for implantation in a patient, the assembly comprising:
   an electrode adapted for insertion into a chamber of the patient's heart for electrical stimulation thereof and having a lumen extending through the electrode from a proximal end to a distal end thereof;
   a lead connected to said proximal end of the electrode at a distal end of the lead and adapted to transmit electrical impulses between the electrode and a proximal end of the lead, the lead having a lumen extending through the lead from the proximal end to the distal end thereof;
   fixation means for securing the electrode to the lining of the heart chamber, the fixation means being in the lumen of the electrode and having a bore at a proximal side of said fixation means; and
   a stylet having a flexible tube and a flexible wire with an enlarged tip at a distal end of the wire, the wire being adapted to be slidingly received within said flexible tube, the distal end of said wire and a distal end of said tube being adapted to be placed within said bore and the enlarged tip being adapted to be wedged into said tube to secure the distal end of the stylet within the bore.

2. The lead assembly according to claim 1 wherein the fixation means comprises a sharpened helix.

3. The lead assembly according to claim 2 further comprising means for preventing the sharpened helix from rotating with respect to the electrode.

4. The lead assembly according to claim 3 wherein the rotation preventing means comprise an hexagonal inner surface on the electrode and a mating hexagonal outer surface on the fixation means.

5. The lead assembly according to claim 1 wherein the flexible tube comprises a polyamide tube.

6. The lead assembly according to claim 1 wherein the enlarged tip comprises a soldered metal bulb.

7. The lead assembly according to claim 6 wherein the metal bulb has an outside diameter substantially equal to an outside diameter of said tube.

8. The lead assembly according to claim 7 wherein the metal bulb comprises a tapered proximal edge adapted to wedge into said tube.

9. The lead assembly according to claim 1 wherein the enlarged tip has an outside diameter substantially equal to an outside diameter of said tube.

10. The lead assembly according to claim 9 wherein the enlarged tip comprises a tapered proximal edge adapted to wedge into said tube.

* * * * *